United States Patent
Mest

(10) Patent No.: US 8,287,531 B2
(45) Date of Patent: *Oct. 16, 2012

(54) CATHETER WITH ABLATION NEEDLE AND MAPPING ASSEMBLY

(75) Inventor: Robert A. Mest, Long Beach, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 1112 days.

This patent is subject to a terminal disclaimer.

(21) Appl. No.: 12/140,996

(22) Filed: Jun. 17, 2008

(65) Prior Publication Data

US 2008/0249392 A1 Oct. 9, 2008

Related U.S. Application Data

(63) Continuation of application No. 11/322,603, filed on Dec. 30, 2005, now Pat. No. 7,387,630, which is a continuation of application No. 10/693,553, filed on Oct. 24, 2003, now Pat. No. 7,179,256.

(51) Int. Cl.
*A61B 18/14* (2006.01)
*A61F 2/00* (2006.01)

(52) U.S. Cl. .......................................... 606/41; 607/101
(58) Field of Classification Search .................... 606/42, 606/41; 607/101
See application file for complete search history.

(56) References Cited

U.S. PATENT DOCUMENTS

| | | |
|---|---|---|
| 5,551,426 A | 9/1996 | Hummel et al. |
| 5,702,438 A | 12/1997 | Avitall |
| 5,782,239 A | 7/1998 | Webster, Jr. |
| 5,782,889 A | 7/1998 | Hognelid et al. |
| 5,800,484 A | 9/1998 | Gough et al. |
| 5,938,694 A | 8/1999 | Jaraczewski et al. |
| 6,014,579 A | 1/2000 | Pomeranz et al. |

(Continued)

FOREIGN PATENT DOCUMENTS

EP 1 205 156 A2 5/2002

(Continued)

OTHER PUBLICATIONS

EPO Search Report dated Jan. 31, 2005 for European Patent Application No. 04256538.1.

*Primary Examiner* — Roy Gibson
*Assistant Examiner* — Jared W Pike
(74) *Attorney, Agent, or Firm* — Christie, Parker & Hale, LLP

(57) ABSTRACT

The invention is directed to a catheter that creates enhanced lesions using a needle electrode and can simultaneously map electrical activity at a plurality of points using an enhanced mapping assembly. The catheter comprises an elongated catheter body having at least one lumen extending longitudinally therethrough. A needle control handle is provided at the proximal end of the catheter body. A needle electrode assembly extends through the catheter body and needle control handle and has a proximal end attached to the needle control handle and a distal end within the distal end of the catheter body. A mapping assembly is mounted at the distal end of the catheter body and comprises at least two flexible spines. Each spine has a proximal end attached at the distal end of the catheter body and a free distal end. Each spine carries at least one electrode. The distal end of the needle electrode assembly is extendable past the proximal end of the mapping assembly upon manipulation of the needle control handle.

20 Claims, 11 Drawing Sheets

U.S. PATENT DOCUMENTS

| | | | |
|---|---|---|---|
| 6,053,937 A | 4/2000 | Edwards et al. | |
| 6,286,512 B1 | 9/2001 | Loeb et al. | |
| 6,330,478 B1 | 12/2001 | Lee et al. | |
| 6,574,492 B1* | 6/2003 | Ben-Haim et al. | 600/374 |
| 6,748,255 B2 | 6/2004 | Fuimaono et al. | |
| 6,961,602 B2 | 11/2005 | Fuimaono et al. | |
| 7,179,256 B2* | 2/2007 | Mest | 606/41 |
| 7,387,630 B2* | 6/2008 | Mest | 606/41 |
| 2003/0010987 A1 | 1/2003 | Banin et al. | |
| 2003/0109871 A1 | 6/2003 | Johnson et al. | |
| 2003/0125614 A1* | 7/2003 | Fuimaono et al. | 600/374 |
| 2004/0044277 A1 | 3/2004 | Fuimaono et al. | |
| 2004/0087848 A1 | 5/2004 | Mejia | |
| 2005/0090729 A1 | 4/2005 | Solis et al. | |
| 2006/0106377 A1 | 5/2006 | Mest | |

FOREIGN PATENT DOCUMENTS

| | | |
|---|---|---|
| EP | 1297796 | 4/2003 |
| WO | WO 02/054941 | 7/2002 |

* cited by examiner

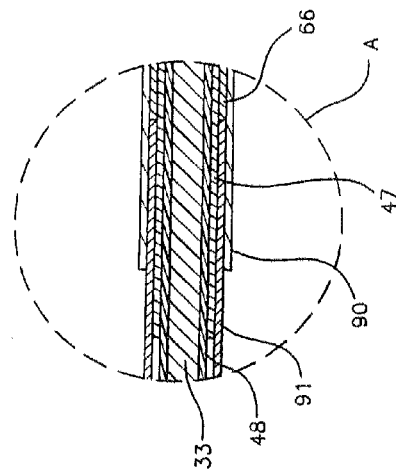
FIG. 2A (AREA A)
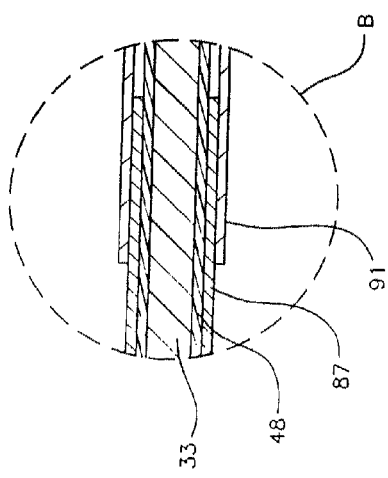
FIG. 2B (AREA B)
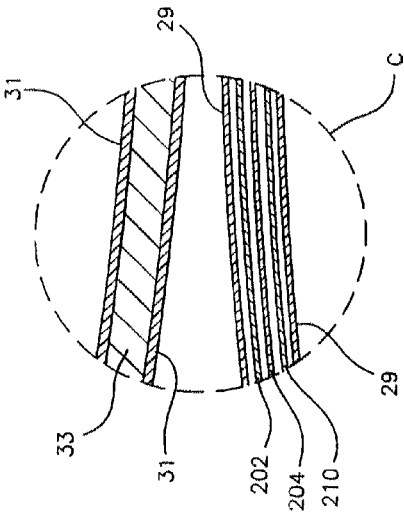
FIG. 2C (AREA C)

CATHETER WITH ABLATION NEEDLE AND MAPPING ASSEMBLY

CROSS-REFERENCE TO RELATED APPLICATION(S)

This application is a continuation of U.S. patent application Ser. No. 11/322,603, entitled CATHETER WITH ABLATION NEEDLE AND MAPPING ASSEMBLY, filed on Dec. 30, 2005, now U.S. Pat. No. 7,387,630 which is a continuation of U.S. patent application Ser. No. 10/693,553, entitled CATHETER WITH ABLATION NEEDLE AND MAPPING ASSEMBLY, filed Oct. 24, 2003, now U.S. Pat. No. 7,179,256 the entire contents of which is incorporated herein by reference.

BACKGROUND OF THE INVENTION

Radiofrequency (RF) ablation of cardiac and other tissue is a well known method for creating thermal injury lesions at the tip of an electrode. Radiofrequency current is delivered between a skin (ground) patch and the electrode. Electrical resistance at the electrode-tissue interface results in direct resistive heating of a small area, the size of which depends upon the size of the electrode, electrode tissue contact, and current (density). See Avitall B, Helms R. Determinants or Radiofrequency-Induced Lesion Size in Huang S K S, Wilber D J (eds.): Radiofrequency Catheter Ablation of Cardiac Arrhythmias: Basic Concepts and Clinical Applications, $2^{nd}$ ed. Armonk, N.Y., Futura Publishing Company, Inc., 2000: 47-80. Further tissue heating results from conduction of heat within the tissue to a larger zone. Tissue heated beyond a threshold of approximately 50-55° C. is irreversibly injured (ablated). See Nath S, and Haines D E. Pathophysiology of Lesion Formation by Radiofrequency Catheter Ablation, in Huang S K S, Wilber D J (eds.): Radiofrequency Catheter Ablation of Cardiac Arrhythmias: Basic Concepts and Clinical Applications, $2^{nd}$ ed. Armonk, N.Y., Futura Publishing Company, Inc., 2000:26-28.

Resistive heating is caused by energy absorption due to electrical resistance. Energy absorption is related to the square of current density and inversely with tissue conductivity. Current density varies with conductivity and voltage and inversely with the square of radius from the ablating electrode. Therefore, energy absorption varies with conductivity, the square of applied voltage, and inversely with the fourth power of radius from the electrode. Resistive heating, therefore, is most heavily influenced by radius, and penetrates a very small distance from the ablating electrode. The rest of the lesion is created by thermal conduction from the area of resistive heating. See Lin J, Physical Aspects of Radiofrequency Ablation, in Huang S K S, Wilber D J (eds.): Radiofrequency Catheter Ablation of Cardiac Arrhythmias: Basic Concepts and Clinical Applications, $2^{nd}$ ed. Armonk, N.Y., Futura Publishing Company, Inc., 2000:14-17. This imposes a limit on the size of ablation lesions that can be delivered from a surface electrode.

Theoretical methods to increase lesion size would include increasing electrode diameter, increasing the area of electrode contact with tissue, increasing tissue conductivity and penetrating the tissue to achieve greater depth and increase the area of contact, and delivering RF until maximal lesion size has been achieved (60-90 seconds for full maturation).

The electrode can be introduced to the tissue of interest directly (for superficial/skin structures), surgically, endoscopically, laparoscopically or using percutaneous transvascular (catheter-based) access. Catheter ablation is a well-described and commonly performed method by which many cardiac arrhythmias are treated. See Miller J M, Zipes D P. Management of the Patient with Cardiac Arrhythmias. In Braunwald E, Zipes D, Libby P (eds): Heart Disease: A Textbook of Cardiovascular Medicine, $6^{th}$ Ed. Philadelphia, Pa., W.B. Saunders Company, 2001: p742-752. Needle electrodes have been described for percutaneous or endoscopic ablation of solid-organ tumours, lung tumours, and abnormal neurologic structures. See, for example, McGahan J P, Schneider P, Brock J M, Tesluk H. Treatment of Liver Tumors by Percutaneous Radiofrequency Electrocautery. Seminars in Interventional Radiology 1993; 10:143-149; Rossi S, Fomari F, Buscarini L. Percutaneous Ultrasound-Guided Radiofrequency Electrocautery for the Treatment of Small Hepatocellular Carcinoma. J Intervent Radiol 1993; 8:97-103; and Livraghi T, Goldberg S N, Lazzaroni S, Meloni F, Monti F, Solbiati L. Saline-enhanced RF tissue ablation in the treatment of liver Metastases. Radiology 1995; 197(P):140 (abstr)].

Catheter ablation is sometimes limited by insufficient lesion size. See de Bakker J M T, van Capelle F J L, Janse M J et al. Macroreentry in the infarcted human heart: mechanism of ventricular tacycardias with a "focal" activation pattern. J Am Coll Cardiol 1991; 18:1005-1014; Kaltenbrunner W, Cardinal R, Dubuc M et al. Epicardial and endocardial mapping of ventricular tachycardia in patients with myocardial infarction. Is the origin of the tachycardia always subendocardially localized? Circulation 1991; 84:1058-1071. Stevenson W G, Friedman P L, Sager P T et al. Exploring postinfarction reentrant ventricular tachycardia with entrainment mapping. J Am coll Cardiol 1997; 29:1180-1189. Ablation of tissue from an endovascular approach results not only in heating of tissue, but of heating of the electrode. When the electrode reaches critical temperatures, denaturation of blood proteins causes coagulum formation. Impedance can then rise and limit current delivery. Within tissue, overheating can cause evaporation of tissue or blood water and steam bubble formation (steam "pops") with risk of uncontrolled tissue destruction or undesirable perforation of bodily structures. In cardiac ablation, clinical success is sometimes hampered by inadequate lesion depth and transverse diameter even when using catheters with active cooling of the tip. See Soejima K, Delacretaz E, Suzuki M et al. Saline-cooled versus standard radiofrequency catheter ablation for infarct-related ventricular tachycardias. Circulation 2001; 103:1858-1862. Theoretical solutions have included increasing the electrode size (increasing contact surface and increasing convective cooling by blood flow), improving electrode-tissue contact, actively cooling the electrode with fluid infusion, changing the material composition of the electrode to improve current delivery to tissue, and pulsing current delivery to allow intermittent cooling.

Needle electrodes improve contact with tissue and allow deep penetration of current delivery to areas of interest. Ablation may still be hampered by the small surface area of the needle electrode such that heating occurs at low power, and small lesions are created.

Additionally, it is desirable to map the electrical activity in the heart before, during or after ablation. If the mapping can be performed with the same catheter used for ablation, the user avoids the need for catheter exchange. Moreover, it is desirable to include a mapping assembly on the catheter comprising a plurality of electrodes that can be used to simultaneously map electrical activity at different positions within the heart to provide more efficient mapping.

SUMMARY OF THE INVENTION

The present invention addresses the above concerns by providing a catheter that creates enhanced lesions using a needle electrode and can simultaneously map electrical activity at a plurality of points using an enhanced mapping assembly. The catheter comprises an elongated catheter body having at least one lumen extending longitudinally therethrough. A needle control handle is provided at the proximal end of the catheter body. A needle electrode assembly extends through the catheter body and needle control handle and has a proximal end attached to the needle control handle and a distal end within the distal end of the catheter body. A mapping assembly is mounted at the distal end of the catheter body and comprises at least two flexible spines. Each spine has a proximal end attached at the distal end of the catheter body and a free distal end. Each spine carries at least one electrode. The distal end of the needle electrode assembly is extendable past the proximal end of the mapping assembly upon manipulation of the needle control handle.

BRIEF DESCRIPTION OF THE DRAWINGS

These and other features and advantages of the present invention will be better understood by reference to the following detailed description when considered in conjunction with the accompanying drawings wherein:

FIG. 2A is an enlarged close-up view of Area A in FIG. 2.

FIG. 2B is an enlarged close-up view of Area B in FIG. 2.

FIG. 2C is an enlarged close-up view of Area C in FIG. 2.

DETAILED DESCRIPTION OF THE INVENTION

Figure 1:
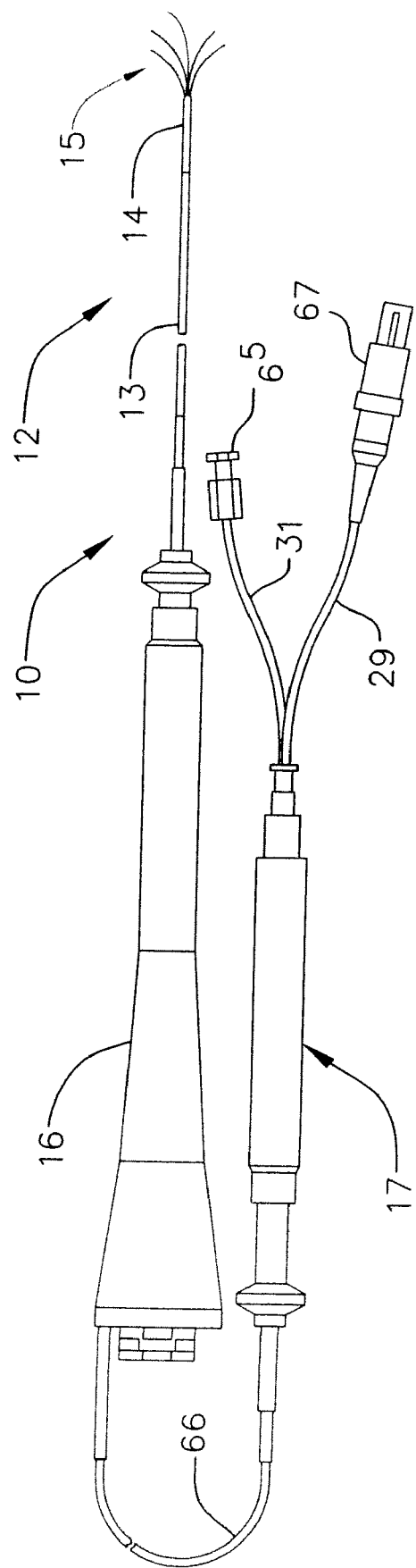
FIG. 1 is a side plan view of an embodiment of a catheter of the present invention.

As shown in FIG. 1, the catheter 10 comprises an elongated catheter body 12 having a proximal shaft 13 and a distal shaft 14, a mapping assembly 15 mounted at the distal end of the distal shaft, a deflection control handle 16 attached to the proximal end of the proximal shaft, and a needle control handle 17 attached indirectly to the catheter body proximal to the deflection control handle.

Figure 5:
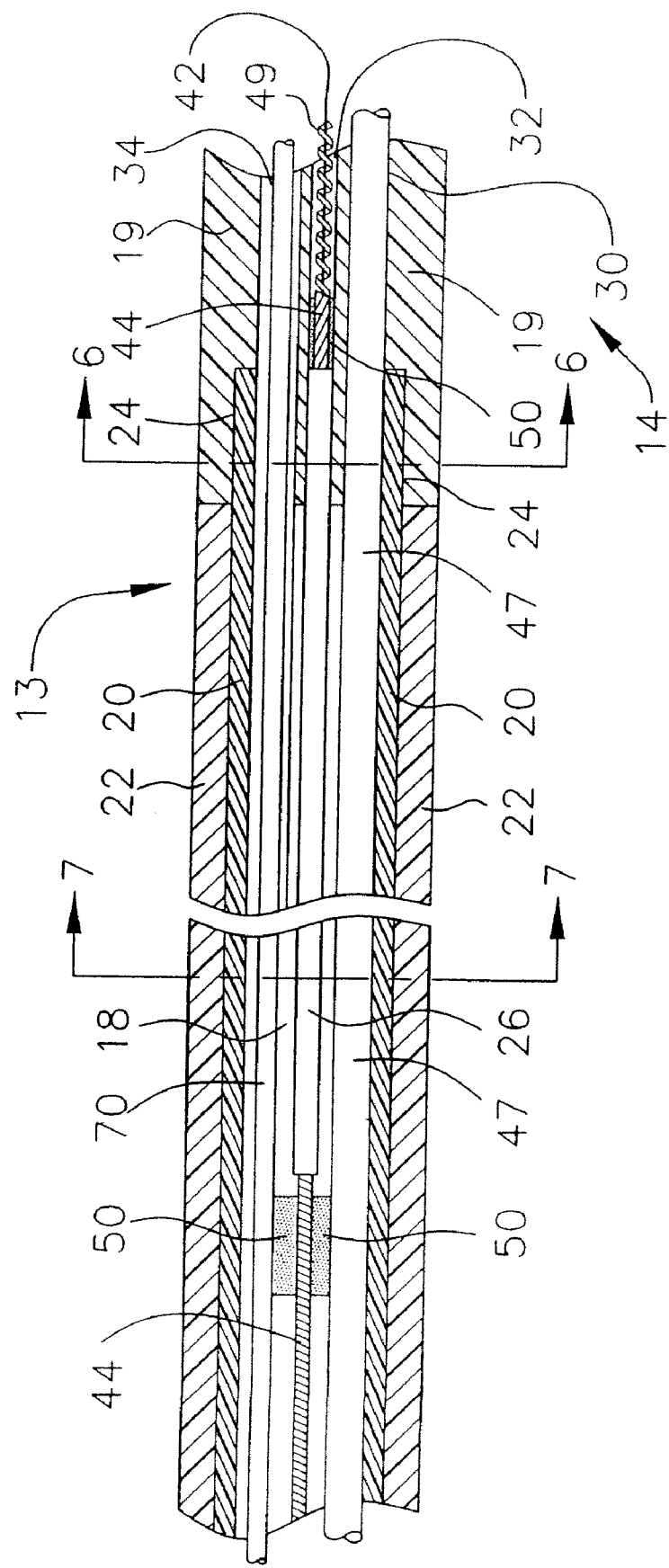
FIG. 5 is a side cross-sectional view of the catheter body, including the junction between the proximal shaft and the distal shaft.
Figure 7:
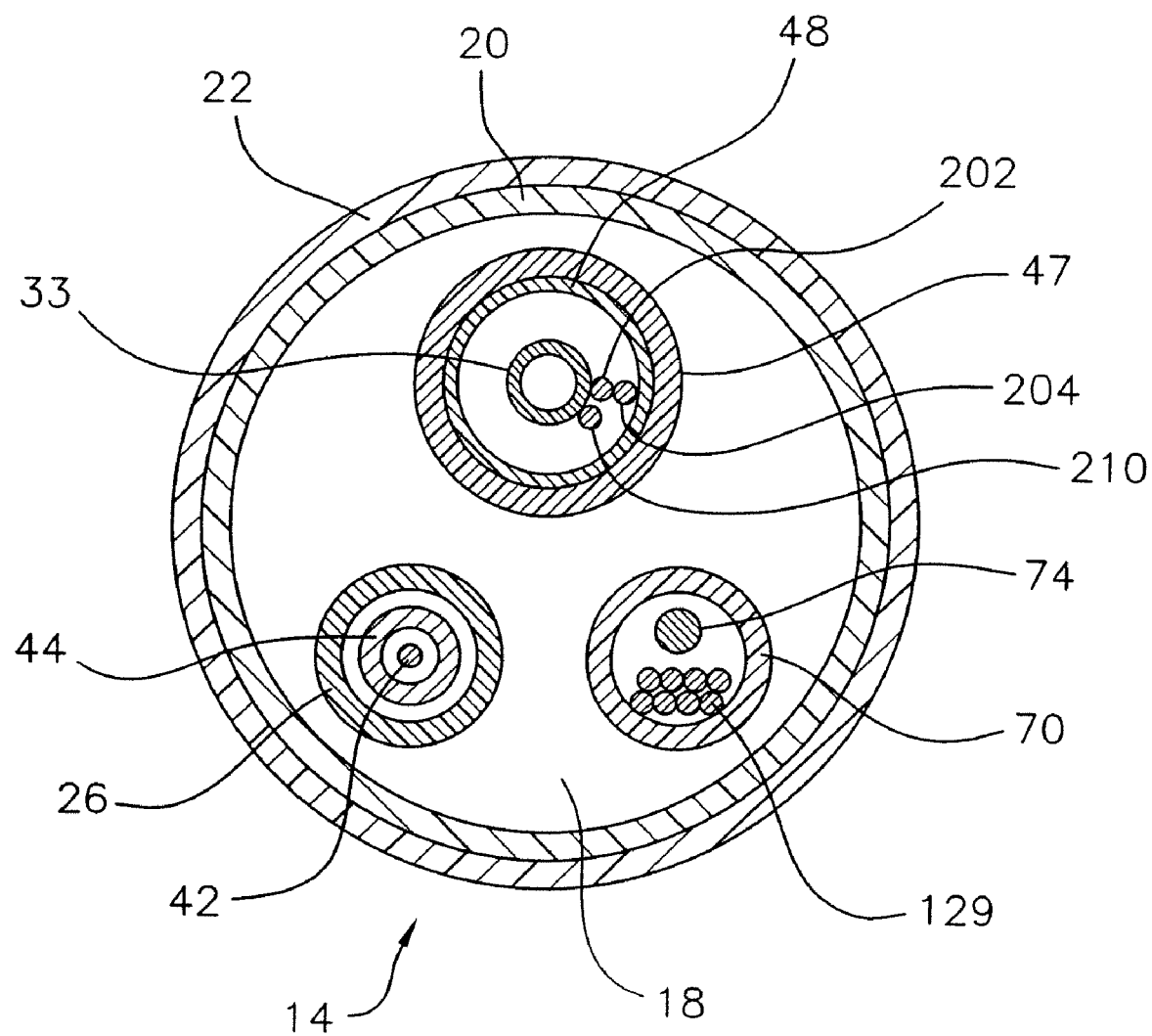
FIG. 7 is an end cross-sectional view of the proximal shaft of the catheter body shown in FIG. 5 along line 7-7.

With reference to FIGS. 5 and 7, the proximal shaft 13 comprises a single, central or axial lumen 18. The proximal shaft 13 is flexible, i.e., bendable, but substantially non-compressible along its length. The proximal shaft 13 may be of any suitable construction and made of any suitable material. A presently preferred construction comprises an outer wall 22 made of polyurethane or nylon. The outer wall 22 comprises an imbedded braided mesh of stainless steel or the like to increase torsional stiffness of the proximal shaft 13 so that, when the deflection control handle 16 is rotated, the distal shaft 14 of the catheter 10 will rotate in a corresponding manner.

The outer diameter of the proximal shaft 13 is not critical, but is preferably no more than about 8 French. Likewise the thickness of the outer wall 22 is not critical. In the depicted embodiment, the inner surface of the outer wall 22 is lined with a stiffening tube 20, which can be made of any suitable material, preferably polyimide. The stiffening tube 20, along with the braided outer wall 22, provides improved torsional stability while at the same time minimizing the wall thickness of the catheter, thus maximizing the diameter of the single lumen. The outer diameter of the stiffening tube 20 is about the same as or slightly smaller than the inner diameter of the outer wall 22.

Figure 6:
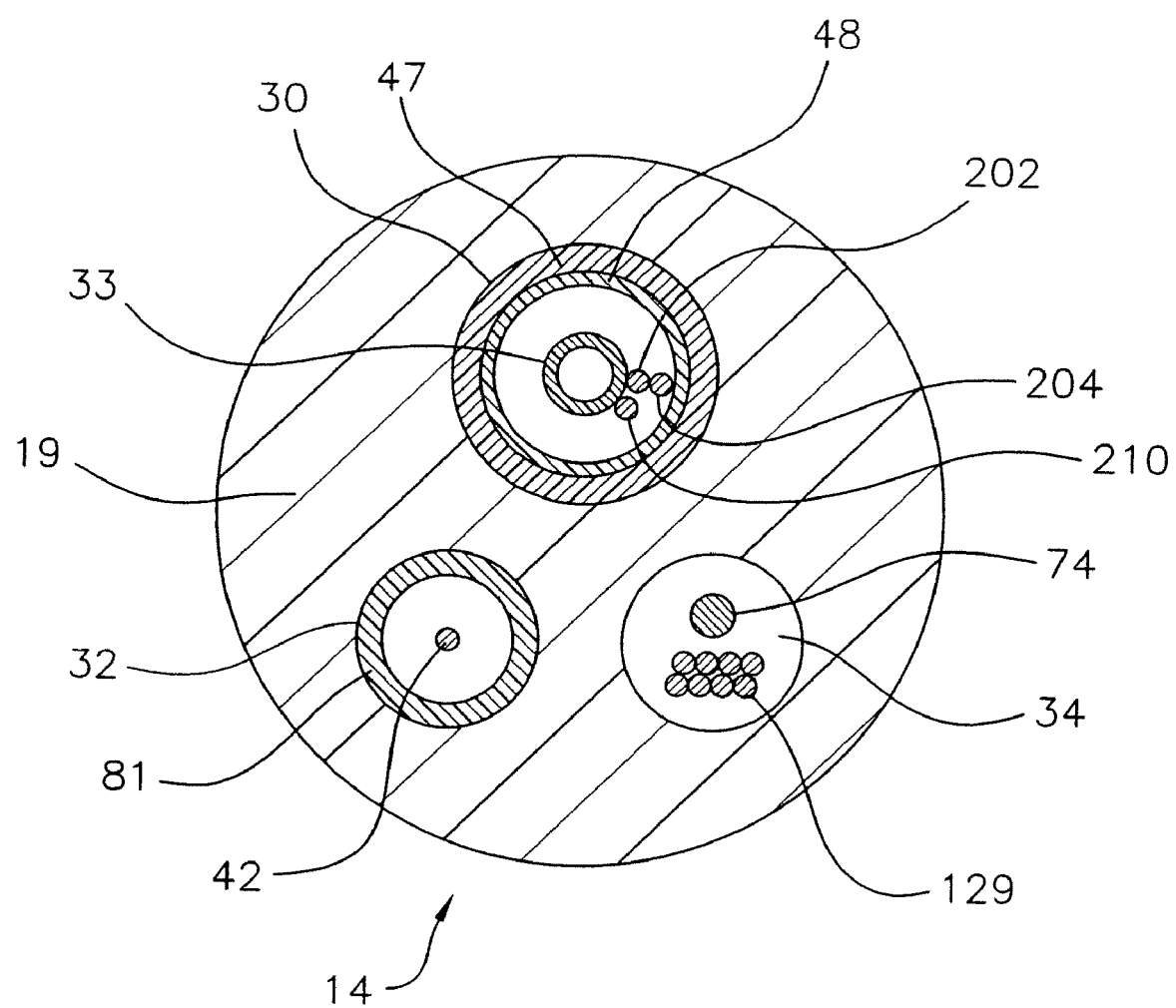
FIG. 6 is an end cross-sectional view of the distal shaft of the catheter body shown in FIG. 5 along line 6-6.

As shown in FIGS. 5 and 6, the distal shaft 14 comprises a short section of tubing 19 having three lumens, namely an infusion lumen 30, a puller wire lumen 32 and a lead wire lumen 34. The tubing 19 is made of a suitable non-toxic material that is preferably more flexible than the proximal shaft 13. A presently preferred material for the tubing 19 is braided polyurethane, i.e., polyurethane with an embedded mesh of braided stainless steel or the like. The outer diameter of the distal shaft 14, like that of the proximal shaft 13, is preferably no greater than about 8 French.

A preferred means for attaching the proximal shaft 13 to the distal shaft 14 is illustrated in FIG. 5. The proximal end of the distal shaft 14 comprises an inner counter bore 24 that receives the outer surface of the stiffener 20. The distal shaft 14 and proximal shaft 13 are attached by glue or the like. Other methods for attaching the proximal shaft 13 to the distal shaft 14 can be used in accordance with the invention.

The stiffening tube 20 is held in place relative to the outer wall 22 at the proximal shaft 13. In a preferred construction of the proximal shaft 13, a force is applied to the proximal end of the stiffening tube 20, which causes the distal end of the stiffening tube 20 to firmly push against the counter bore 24. While under compression, a first glue joint is made between the stiffening tube 20 and the outer wall 22 by a fast drying glue, e.g. Super Glue®. Thereafter a second glue joint is formed between the proximal ends of the stiffening tube 20 and outer wall 22 using a slower drying but stronger glue, e.g., polyurethane.

The depicted catheter includes a mechanism for deflecting the distal shaft 14 of the catheter body 12. In the depicted embodiment, a puller wire 42 extends into the puller wire lumen 32 of the distal shaft 14. The puller wire 42 is anchored at its proximal end to the deflection control handle 16 and anchored at its distal end to the distal shaft 14. The puller wire 42 is made of any suitable metal, such as stainless steel or Nitinol, and is preferably coated with Teflon® or the like. The coating imparts lubricity to the puller wire 42. The puller wire 42 preferably has a diameter ranging from about 0.006 to about 0.010 inches.

Referring to FIG. 5, the compression coil 44 extends from the proximal end of the proximal shaft 13 to the proximal end of the distal shaft 14. The compression coil 44 is made of any suitable metal, preferably stainless steel. The compression coil 44 is tightly wound on itself to provide flexibility, i.e., bending, but to resist compression. The inner diameter of the compression coil 44 is preferably slightly larger than the diameter of the puller wire 42. For example, when the puller wire 42 has a diameter of about 0.007 inches, the compression coil 44 preferably has an inner diameter of about 0.008 inches. The Teflon® coating on the puller wire 42 allows it to slide freely within the compression coil 44. Along its length, the outer surface of the compression coil 44 is covered by a flexible, non-conductive sheath 26 to prevent contact between the compression coil 44 and any of the lead wires 129 or needle electrode assembly 46. A non-conductive sheath 26 made of polyimide tubing is presently preferred. As shown in FIG. 5, the compression coil 44 is anchored at its proximal end to the proximal end of the stiffening tube 20 in the proximal shaft 13 by glue to form a glue joint 50 and at its distal end to the distal shaft 14 in the puller wire lumen 32.

Figure 10:
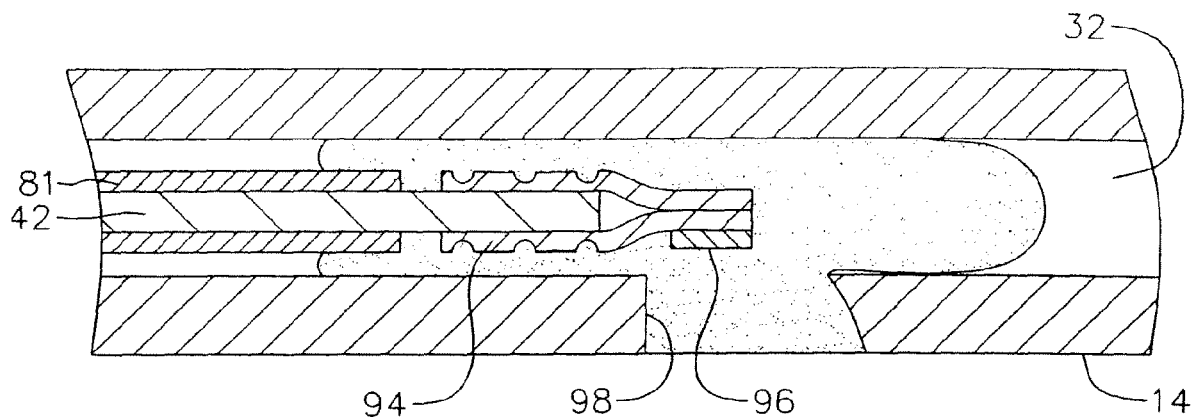
FIG. 10 is a side cross sectional view of a portion of the catheter tip section showing one means for attaching the puller wire.
Figure 11:
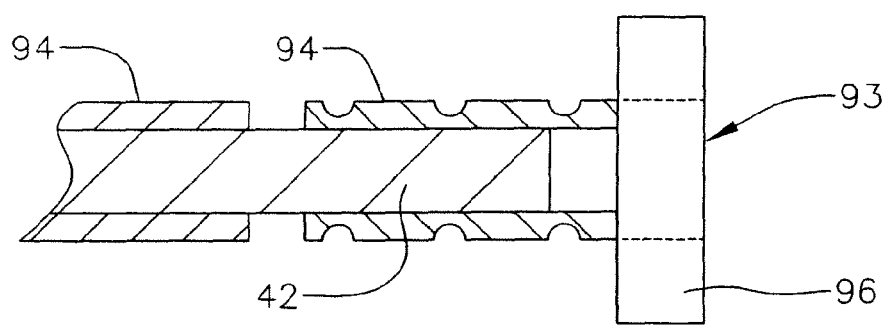
FIG. 11 is a top cross sectional views of a preferred puller wire anchor.
Figure 12:
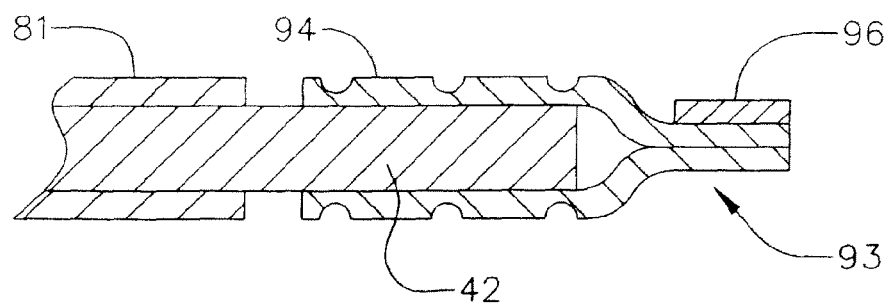
FIG. 12 is a side cross sectional views of the puller wire anchor of FIG. 11.

The puller wire 42 extends into the puller wire lumen 32 of the distal shaft 14. Preferably the puller wire 42 is anchored at its distal end to the side of the distal shaft 14, as shown in FIGS. 10 to 12. In this embodiment, a T-shaped anchor 93 is formed which comprises a short piece of tubular stainless steel 94, e.g., hypodermic stock, which is fitted over the distal end of the puller wire 42 and crimped to fixedly secure it to the puller wire. The distal end of the tubular stainless steel 94 is fixedly attached, e.g., by welding, to a stainless steel cross-piece 96, such as stainless steel ribbon or the like. The cross-piece 96 sits in a notch 98 in a wall of the distal shaft 14 that extends into the second lumen 32. The stainless steel cross-piece 96 is larger than the notch 98 and, therefore, cannot be pulled through the notch. The portion of the notch 98 not filled by the cross-piece 96 is filled with glue or the like, preferably a polyurethane glue, which is harder than the material of the distal shaft 14. Rough edges, if any, of the cross-piece 96 are polished to provide a smooth, continuous surface with the outer surface of the distal shaft 14.

With further reference to FIG. 5, within the distal shaft 14, and distal to the glue joint 50, the turns of the compression coil are expanded longitudinally. Such expanded turns 49 are both bendable and compressible and preferably extend for a length of about 0.5 inch. The puller wire 42 extends through the expanded turns 49 then into a plastic, preferably Teflon®, sheath 81, which prevents the puller wire from cutting into the wall of the distal shaft 14 when the distal shaft is deflected.

Any other suitable technique for anchoring the puller wire 42 in the distal shaft 14 can also be used. Alternatively, other means for deflecting the distal region can be provided, such as the deflection mechanism described in U.S. Pat. No. 5,537,686, the disclosure of which is incorporated herein by reference.

Longitudinal movement of the puller wire 42 relative to the catheter body 12, which results in deflection of the distal shaft 14, is accomplished by suitable manipulation of the control handle 16. Examples of suitable control handles for use in the present invention are disclosed, for example, in U.S. Pat. Nos. Re 34,502, 5,897,529 and 6,575,931, the entire disclosures of which are incorporated herein by reference.

If desired, the catheter can include two or more puller wires (not shown) to enhance the ability to manipulate the distal shaft 14. In such an embodiment, a second puller wire and a surrounding second compression coil extend through the proximal shaft 13 and into separate off-axis lumens (not shown) in the distal shaft. Suitable deflection control handles for use with a catheter having more than one puller wire are described in U.S. Pat. Nos. 6,123,699, 6,171,277, and 6,183,463, the disclosures of which are incorporated herein by reference.

Figure 3:
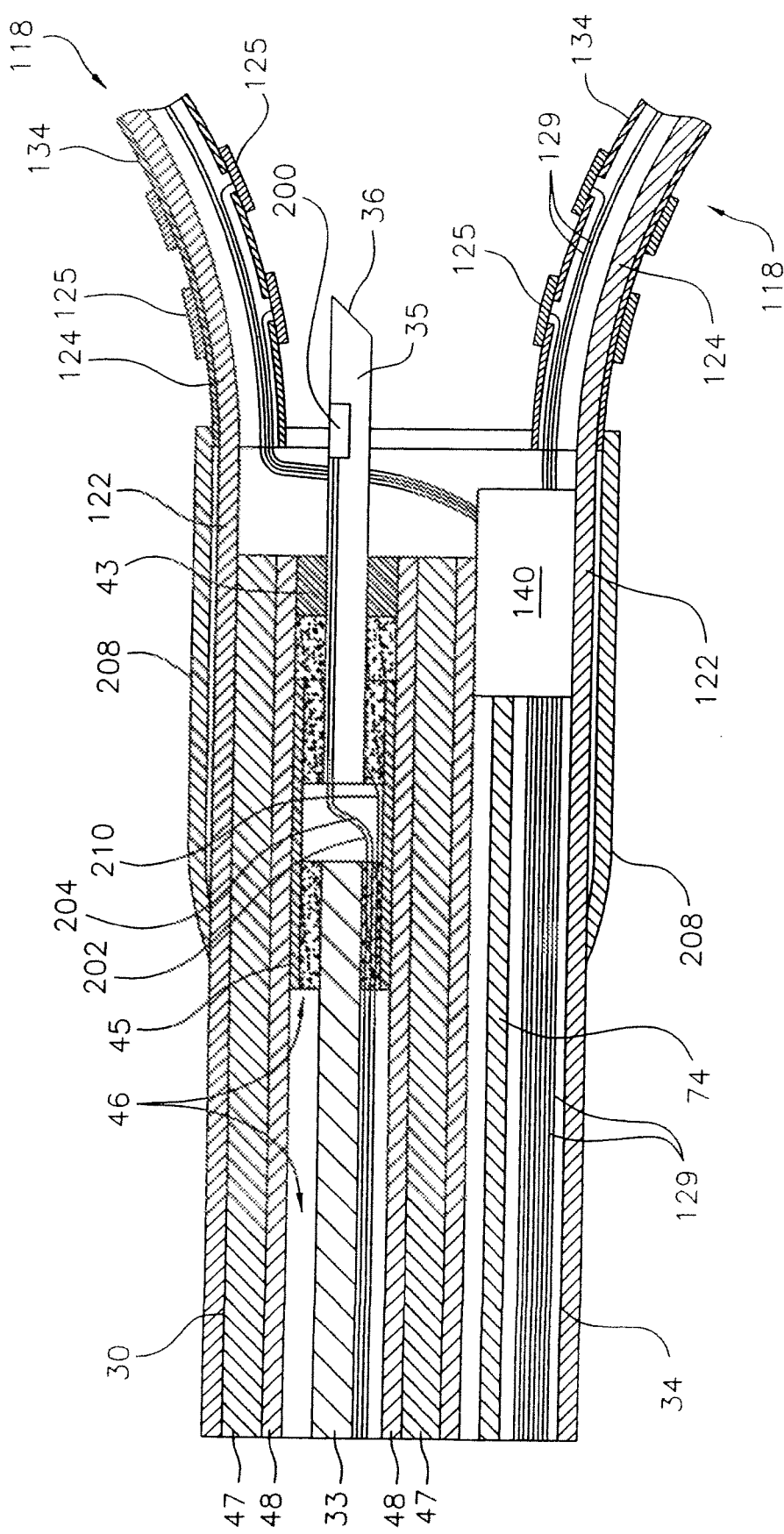
FIG. 3 is a schematic side cross-sectional view of the distal end of the distal shaft, including the proximal end of the mapping assembly.

As shown in FIG. 3, a needle electrode assembly 46 is provided. The needle electrode assembly 46 is used to ablate tissue while simultaneously injecting saline or other fluid to conduct the ablation energy, thereby creating a theoretic increase in the effective size of the electrode. The needle electrode assembly 46 is extendable and retractable, and may be moved by manipulation of the needle control handle 17, as described further below. FIG. 3 depicts the needle electrode assembly 46 in an extended position as it would be to ablate tissue. The distal end of the needle electrode assembly 46 may be withdrawn into the infusion lumen 30 to avoid injury, particularly during the time that the catheter is inserted through the vasculature of the body and during the time in which the catheter is removed from the body.

The needle electrode assembly 46 comprises a proximal tubing 33 joined, directly or indirectly, to a generally rigid, electrically-conductive distal tubing 35, as shown in FIG. 3. The generally rigid nature of the distal tubing 35 allows it to pierce tissue in order to increase its effectiveness during ablation. In an exemplary embodiment, the distal tubing 35 is formed of Nitinol or stainless steel, and, as illustrated in FIG. 3, is preferably formed with a beveled edge 36 at the distal tip of the needle electrode assembly 46 to enhance its ability to pierce tissue. The proximal tubing 33 is preferably more flexible than the distal tubing 35 to allow the proximal tubing to bend as necessary with the flexible proximal shaft 13 of the catheter body 12, for instance when the catheter is inserted into the vasculature of the body. The proximal tubing 33 of the needle electrode assembly 46 is preferably made of polyimide or polyether etherketone (PEEK), but can be made of any other suitable biocompatible material, such as plastic or metal.

A needle electrode lead wire 210 is electrically connected at its distal end to the electrically-conductive distal tubing 35 for supplying radio frequency energy or other suitable ablation energy to the distal tubing. The needle electrode lead wire 210 is soldered, welded or otherwise attached to the outside of the distal tubing 35, but could be attached elsewhere to the distal tubing. The proximal end of the needle electrode lead wire 210 is attached to a suitable connector 67, which in turn is connected to a suitable source of ablation energy (not shown).

Figure 4:
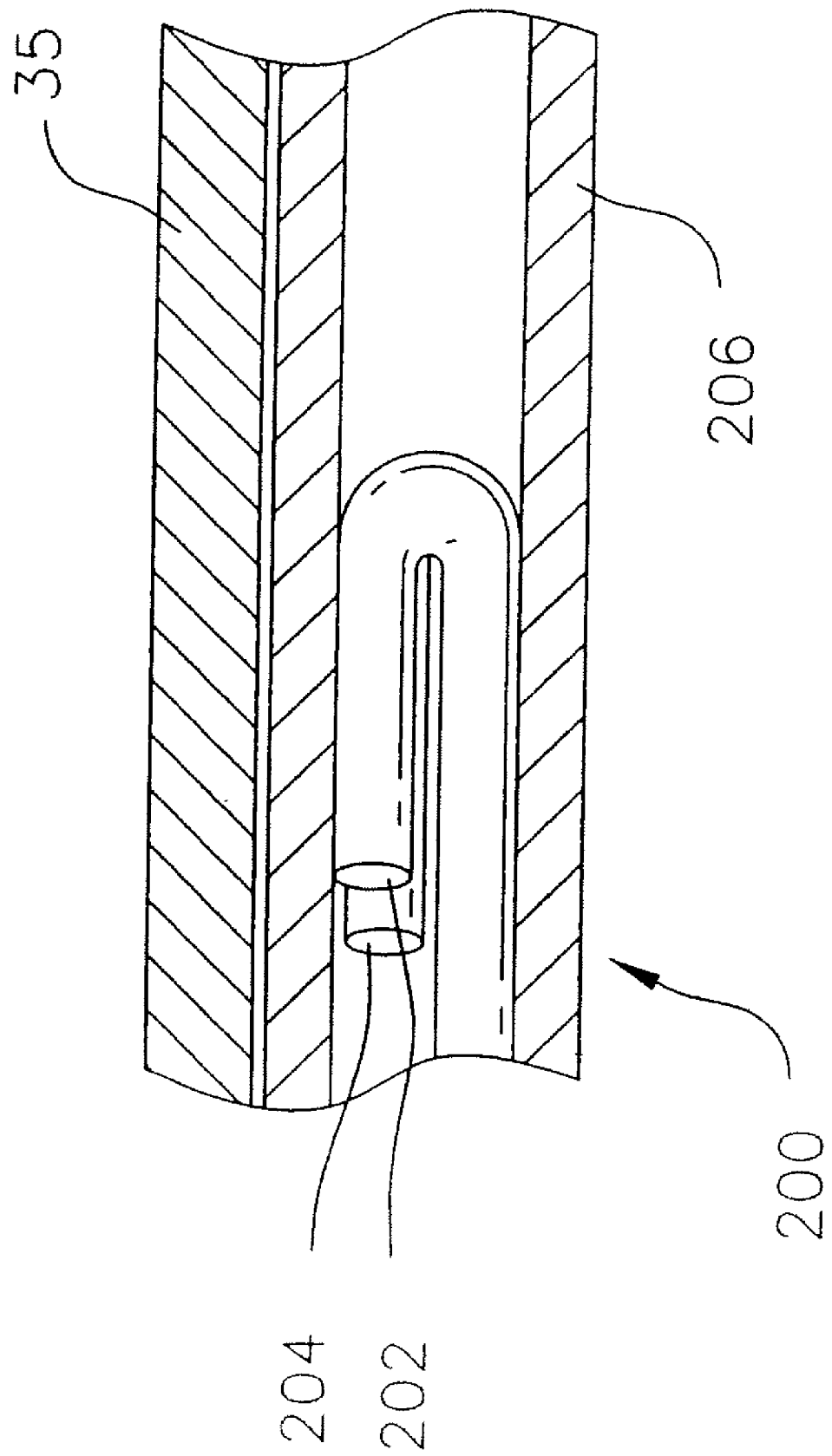
FIG. 4 is a side cross-sectional view of the thermocouple mounted in the needle electrode assembly.

Additionally, a temperature sensor is provided for measuring the temperature of the tissue being ablated by the needle electrode assembly 46 before, during or after ablation. Any conventional temperature sensor, e.g., a thermocouple or thermistor, may be used. In the depicted embodiment, the temperature sensor comprises a thermocouple 200 formed by an enameled wire pair, as best shown in FIG. 4. One wire of the wire pair is a copper wire 202, e.g., a number 40 copper wire. The other wire of the wire pair is a constantan wire 204. The wires 202 and 204 of the wire pair are electrically isolated from each other except at their distal ends, where they are twisted together, covered with a short piece of plastic tubing 206, e.g., polyimide, and covered with epoxy. The plastic tubing 206 is then glued or otherwise attached to the inside wall of the distal tubing 35 of the needle electrode assembly 46, as best shown in FIG. 3. The proximal ends of the wires 202 and 204 extend out the proximal end of the distal tubing 35 and are attached to an appropriate connector (not shown) connectable to a suitable temperature monitor (not shown). In an alternative embodiment, the copper wire 202 of the thermocouple can also be used as the lead wire for the needle electrode assembly 46.

The proximal tubing 33 of the needle electrode assembly 46 extends from the needle control handle 17, through the deflection control handle 16, through the proximal shaft 13, and into the infusion lumen 30 of the distal shaft 14. The proximal end of the distal tubing 35 is spaced slightly from the distal end of the proximal tubing 33 and extends through the infusion lumen 30 of the distal shaft 14. The proximal and distal tubings 33 and 35 are mounted, preferably coaxially, within an outer plastic tube 48. The outer plastic tube 48 can be glued or otherwise attached to the proximal and distal tubings to form a single structure that, as described below, is longitudinally moveable relative to the catheter body 12. The outer plastic tube 48 extends through the catheter body 12 with the proximal tubing and protects the needle electrode lead wire 210 and thermocouple wires 202 and 204, which extend between the proximal tubing 33 and outer plastic tube 48, when the needle electrode assembly 46 is moved relative to the catheter body. The needle electrode lead wire 210 and thermocouple wires 202 and 204 extend out through a hole (not shown) in the outer plastic tube 48 within the deflection control handle 16 and are attached to appropriate connectors, as noted above.

FIG. 3 shows one arrangement for joining the outer plastic tube 48 to the proximal and distal tubings 33 and 35. Specifically, a small piece of plastic tubing 45, for example, polyimide tubing, is placed over the discontinuity between the proximal and distal tubings 33 and 35 and attached to the proximal and distal tubings by polyurethane glue or the like to form a single infusion passage through which saline or other fluid can pass from the proximal tubing to the distal tubing. The small piece of plastic tubing 45 helps to protect the thermocouple wires 202 and 204 and the needle electrode lead wire 210. A small, preferably non-conductive, spacer 43 is mounted between the distal tubing 35 and the distal end of the outer plastic tube 48, and optionally glued in place. The spacer 43 prevents bodily fluid from entering into the distal end of the needle electrode assembly 46.

In an exemplary embodiment, the proximal tubing 33 of the needle electrode assembly 46 has an inner diameter of 0.014 inch and an outer diameter of 0.016 inch. The distal tubing 35 has an inner diameter of 0.014 inch and an outer diameter of 0.018 inch and a length of about 1.0 inch. Further, the distal tubing 35 extends past the distal end of the distal shaft 14 about 14 mm. The small plastic tubing 45 has an inner diameter of 0.022 inch and an outer diameter of 0.024, the outer plastic tube 48 has an inner diameter of 0.025 inch and an outer diameter of 0.035 inch, and the plastic spacer 43 has an inner diameter of 0.017 inch and an outer diameter of 0.024 inch.

Within the catheter body 12, the needle electrode assembly 46, comprising the proximal tubing 33, distal tubing 35, spacer 43, plastic tubing 45 and outer plastic tube 48, is slidably mounted, preferably coaxially, within a protective tube 47 that is stationary relative to the catheter body. The protective tube 47, which is preferably made of polyimide, serves to prevent the needle electrode assembly 46 from buckling during extension and retraction of the needle electrode assembly relative to the catheter body 12. The protective tube 47 additionally serves to provide a fluid-tight seal surrounding the needle electrode assembly 46. Within the deflection control handle 16, the protective tube 47 and needle electrode assembly 46 extend into a protective shaft 66, which is preferably made of polyurethane.

Other needle electrode assembly designs are contemplated within the scope of the invention. For example, the needle electrode assembly can comprise a single electrically-conductive tube, such as a Nitinol tube, that extends from the needle control handle 17 to the distal end of the catheter. Such a design is described in U.S. patent application Ser. No. 09/711,648, entitled "Injection Catheter with Needle Electrode," the disclosure of which is incorporated herein by reference.

Longitudinal movement of the needle electrode assembly 46 is achieved using the needle control handle 17. The needle electrode assembly 46 and protective tube 47 extend from the deflection control handle 16 to the needle control handle 17 within the protective shaft 66.

Figure 2:
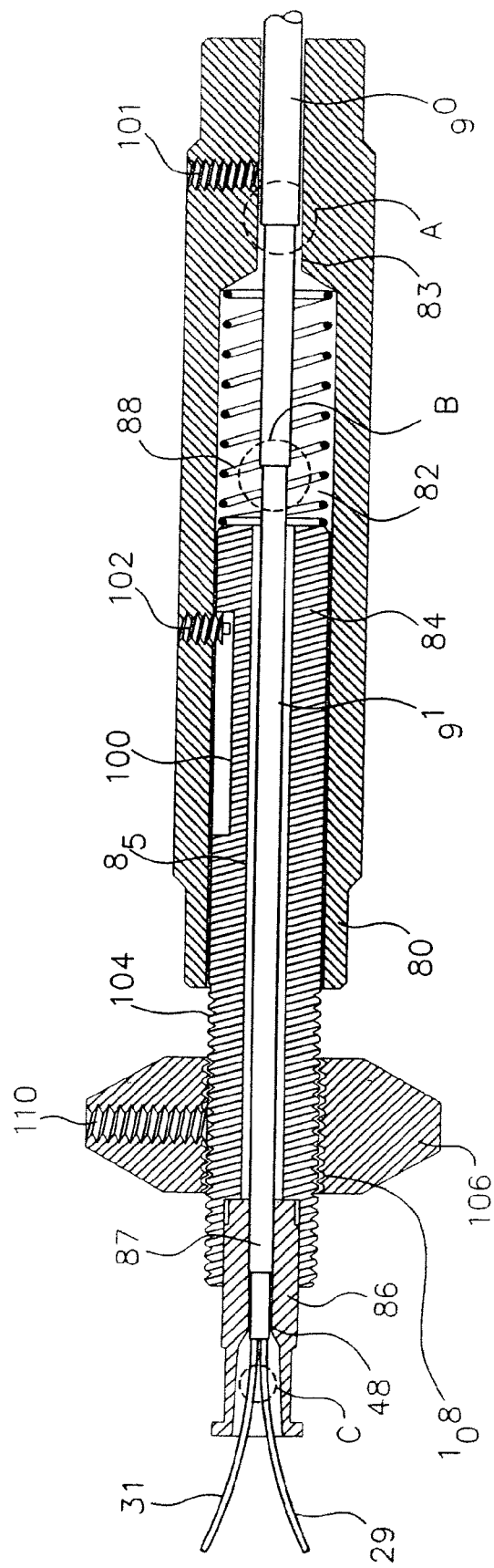
FIG. 2 is a side cross-sectional view of the needle control handle where the needle electrode assembly is in a retracted position.

As illustrated in FIG. 2, in one embodiment the needle control handle 17 comprises a generally cylindrical outer body 80 having proximal and distal ends, a piston chamber 82 extending a part of the way therethrough, and a needle passage 83 extending a part of the way therethrough. The piston chamber 82 extends from the proximal end of the handle part way into the body 80, but does not extend out the distal end of the body. The needle passage 83, which has a diameter less than that of the piston chamber 82, extends from the distal end of the piston chamber to the distal end of the outer body 80.

A piston 84, having proximal and distal ends, is slidably mounted within the piston chamber 82. A proximal fitting 86 is mounted in and fixedly attached to the proximal end of the piston 84. The proximal fitting 86 includes a tubular distal region 87 that extends distally from the main body of the proximal fitting. The piston 84 has an axial passage 85 through which the proximal tubing 33 of the needle electrode assembly 46 extends, as described in more detail below. A compression spring 88 is mounted within the piston chamber 82 between the distal end of the piston 84 and the outer body 80. The compression spring 88 can either be arranged between the piston 84 and outer body 80, or can have one end in contact with or fixed to the piston, while the other end is in contact with or fixed to the outer body.

The proximal tubing 33, outer plastic tube 48, protective tube 47 and protective shaft 66 extend from the deflection control handle 16 into the distal end of the needle passage 83, as best shown in AREA A of FIG. 2. Within the needle passage 83, the proximal tubing 33, outer plastic tube 48, protective tube 47 and protective shaft 66 extend into a first metal tube 90, which is preferably made of stainless steel. If desired, the first metal tube 90 could instead be made of a rigid plastic material. The first metal tube 90 is secured to the outer body 80 of the needle control handle 17 by a set screw 101 or any other suitable means. The protective shaft 66 terminates at its proximal end within the first metal tube 90.

A second metal tube 91 is provided with its distal end mounted, preferably coaxially, inside the proximal end of the first metal tube 90 and with its distal end abutting the proximal end of the protective shaft 66. The second metal tube 91 is fixed in place relative to the first metal tube 90 by the set screw 101. The second metal tube 91, like the first metal tube 90, could alternatively be made of a rigid plastic material.

The proximal end of the second metal tube 91 is mounted, preferably coaxially, around the distal end of the tubular distal region 87 of the proximal fitting 86, with the second metal tube being longitudinally movable relative to the tubular distal region 87. Accordingly, when the piston 84 is moved distally relative to the outer body 80, the tubular distal region 87 moves distally into the second metal tube 91. As shown in AREA B of FIG. 2, the proximal tubing 33 and outer plastic tube 48 extend through the second metal tube 91 and into the tubular distal region 87 of the proximal fitting 86. The outer plastic tube 48 terminates in and is fixedly attached to the proximal fitting 86 to thereby attach the outer plastic tube, and thus the needle electrode assembly 46, to the piston 84. Within the proximal fitting 86, the proximal tubing 33 extends out of the outer plastic tube 48 and into a first protective sheath 31, as shown in AREA C of FIG. 2, and is connected to a luer connector 65, which is connected to an irrigation pump or other suitable fluid infusion source (not shown), as is known in the art. Similarly, the needle electrode lead wire 210 and the thermocouple wires 202 and 204 extend out of the outer plastic tube 48 and into a second protective sheath 29, as also shown in AREA C of FIG. 2, which is connected to a suitable connector 67, such as a 10-pin electrical connector, for connecting the needle electrode lead wire to a source of ablation energy and the thermocouple wires to a suitable monitoring system.

In use, force is applied to the piston 84 to cause distal movement of the piston relative to the outer body 80, which compresses the compression spring 88. This movement causes the needle electrode assembly 46 to correspondingly move distally relative to the outer body 80, protective shaft 66, protective tube 47, proximal shaft 13, and distal shaft 14 so that the distal tubing 35 of the needle electrode assembly extends outside the distal end of the distal shaft. When the force is removed from the piston 84, the compression spring 88 pushes the piston proximally to its original position, thus causing the distal tubing 35 of the needle electrode assembly 46 to retract back into the distal end of the distal shaft 14. Upon distal movement of the piston 84, the tubular distal region 87 of the proximal fitting 86 moves distally into the second metal tube 91 to prevent the proximal tubing 33 and the outer plastic tube 48 of the needle electrode assembly 46 from buckling within the axial passage 85.

The piston 84 further comprises a longitudinal slot 100 extending along a portion of its outer edge. A securing means 102, such as a set screw, pin, or other locking mechanism, extends through the outer body 80 and into the longitudinal slot 100. This design limits the distance that the piston 84 can be slid proximally out of the piston chamber 82. When the needle electrode assembly 46 is in the retracted position, preferably the securing means 102 is at or near the distal end of the longitudinal slot 100.

The proximal end of the piston 84 has a threaded outer surface 104. A circular thumb control 106 is rotatably mounted on the proximal end of the piston 84. The thumb control 106 has a threaded inner surface 108 that interacts with the threaded outer surface 104 of the piston. The thumb control 106 acts as a stop, limiting the distance that the piston 84 can be pushed into the piston chamber 82, and thus the distance that the needle electrode assembly 46 can be extended out of the distal end of the catheter. The threaded surfaces of the thumb control 106 and piston 84 allow the thumb control to be moved closer or farther from the proximal end of the outer body 80 so that the extension distance of the needle electrode assembly 46 can be controlled by the physician. A securing means, such as a tension screw 110 is provided in the thumb control 106 to control the tension between the thumb control and piston 84. As would be recognized by one skilled in the art, the thumb control 106 can be replaced by any other mechanism that can act as a stop for limiting the distance that the piston 84 extends into the piston chamber 82, and it is not necessary, although it is preferred, that the stop be adjustable relative to the piston.

Figure 8:
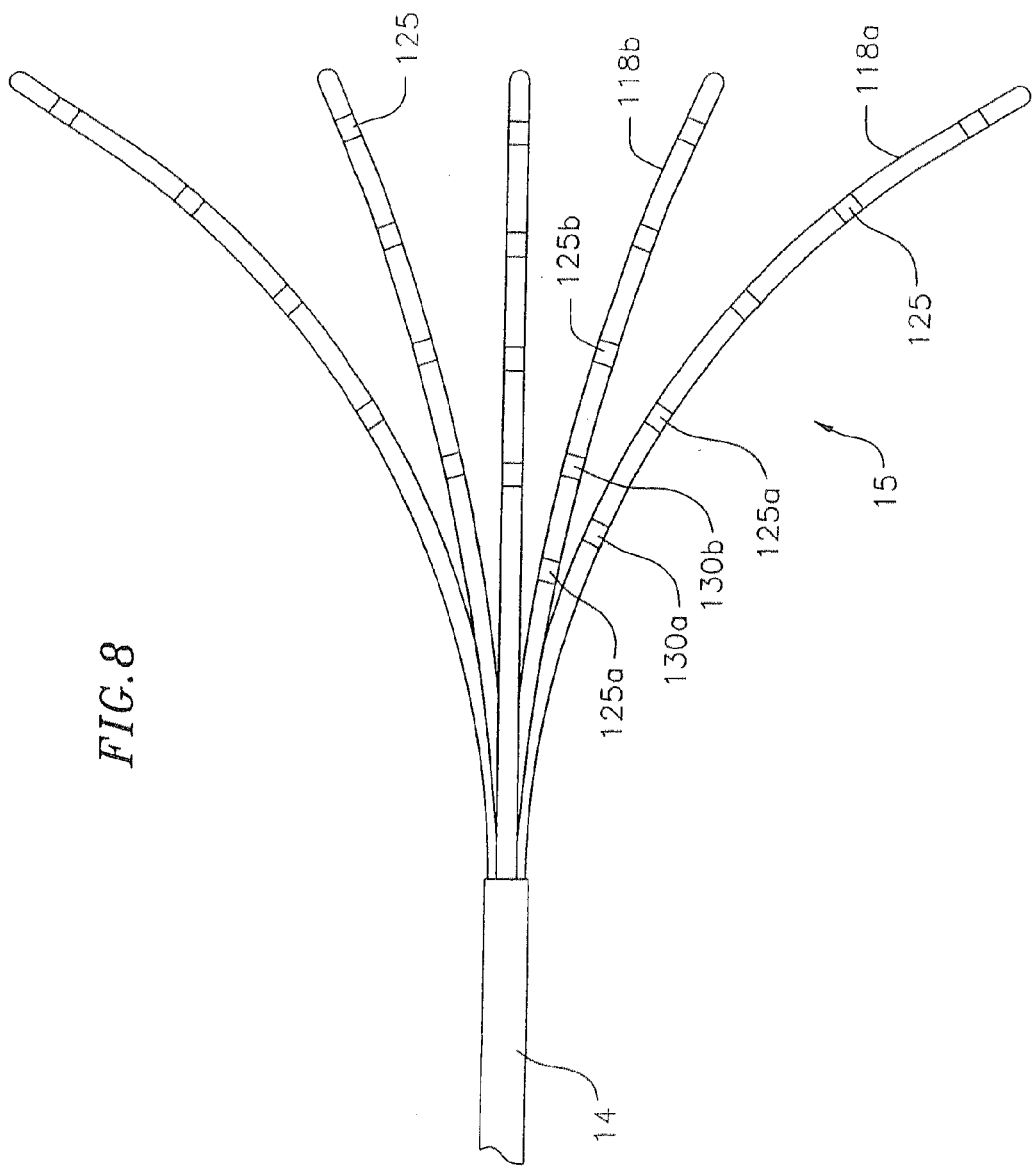
FIG. 8 is a side view of a mapping assembly according to the invention.

As noted above, the mapping assembly 15 is mounted on the distal end of the distal shaft 14. With reference to FIGS. 3 and 8, the mapping assembly 15 comprises two or more flexible spines 118. Each spine 118 has a proximal end attached to the distal end of the catheter body 12 and a free distal end, i.e., the distal end is not attached to any of the other spines, to the catheter body, or to any other structure that confines movement of the distal end of that spine. As will be recognized by one skilled in the art, the number of spines 118 can vary as desired depending on the particular application, so that the mapping assembly 15 has at least two spines, preferably at least three spines, more preferably at least five spines and as many as eight or more spines. The spines 118 are moveable between an expanded arrangement, wherein, for example, each spine arcs outward from the distal end of the catheter body 12, as shown in FIG. 8, and a collapsed arrangement (not shown), wherein, for example, each spine is disposed generally along a longitudinal axis of the catheter body so that the spines are capable of fitting within a lumen of a guiding sheath. As described in more detail below, each spine 118 carries at least one electrode, preferably a ring electrode, such that when the spines are positioned in contact with heart tissue, each spine is capable of obtaining electrical and mechanical data.

In the embodiment shown in FIG. 8, the mapping assembly 15 includes five spines 118, and each spine has a pre-formed configuration in which the spine arcs outwardly from the catheter body 12. However, other spine shapes and configurations are contemplated within the invention. With reference to FIG. 3, each spine 118 comprises a support arm 124 and a non-conductive covering 134 in surrounding relation to the support arm 124. The support arm 124 comprises a metal or plastic material that has shape memory, such that the support arm forms an initial shape (i.e., part of the expanded configuration) when no external forces are applied, forms a deflected shape (e.g., part of the collapsed configuration) when external force is applied, and returns to its initial shape when the external force is released. In one embodiment, each support arm 124 comprises a superelastic material, for example, a nickel-titanium alloy such as nitinol. In a preferred embodiment, the non-conductive covering 134 comprises a biocompatible plastic tubing, such as polyurethane or polyimide tubing. The non-conductive covering 134 may be glued to the support arm 124 or attached indirectly by being glued to the distal end of the distal tubing 35. The non-conductive covering 134 may be attached to the support arm 124 by any other suitable method.

As noted above, each spine 118 carries at least one electrode mounted along its length. In the depicted embodiment, four ring electrodes 125 are mounted on the non-conductive covering 134 of each spine 118, but fewer or additional ring electrodes may be used as desired. Each ring electrode 125 has a length preferably up to about 2 mm, more preferably from about 0.5 mm to about 1 mm. Preferably the ring electrodes 125 are generally evenly-spaced along the length of each spine 118.

Each ring electrode 125 is electrically connected to an electrode lead wire 129, which in turn is electrically connected to a connector (not shown), which can be incorporated into the deflection control handle 16 or provided outside of the catheter. The connector is connected to an appropriate mapping or monitoring system (not shown). Each electrode lead wire 129 extends from the connector, through the deflection control handle 16, through the central lumen 18 in the proximal shaft 13 of the catheter body 12, through the lead wire lumen 34 of the distal shaft 14, and into the non-conductive covering 134 of one of the spines 118, where it is attached to its corresponding ring electrode 125. Within the proximal shaft 13 and deflection control handle 16, the lead wires 129 extend through a protective tube 70, which can be eliminated if desired.

Each lead wire 129, which includes a non-conductive coating over almost all of its length, is attached to its corresponding ring electrode 125 by any suitable method. An exemplary method for attaching a lead wire 129 to a ring electrode 125 involves first making a small hole through an outer wall of the non-conductive covering 134. Such a hole can be created, for example, by inserting a needle through the non-conductive covering 134 and heating the needle sufficiently to form a permanent hole. The lead wire 129 is then drawn through the hole by using a microhook or the like. The end of the lead wire 129 is then stripped of any coating and welded to the underside of the ring electrode 125, which is then slid into position over the hole and fixed in place with polyurethane glue or the like. Alternatively, each ring electrode 125 may be formed by wrapping the lead wire 129 around the non-conductive covering 134 a number of times and stripping the lead wire of its own non-conductive coating on its outwardly facing surfaces. In such an instance, the lead wire 129 functions as a ring electrode.

In the depicted embodiment, two of the spines 118 each carry a marker band 130a, 130b to help the user identify the orientation of the mapping assembly 15 under fluoroscopy. Each marker band 130a, 130b comprises a metal ring (e.g., a ring electrode not attached to a lead wire) of sufficient radiopacity. The marker bands 130 and 130b may be placed along any part of the spine 118, as long as they are not in contact with any of the ring electrodes 125. Preferably, a first marker band 130a is placed on a first spine 118a between the most proximal ring electrode 125a and the distal shaft 14, and a second marker band 130b is placed on a second spine 118b between the most proximal ring electrode 125a and the second most proximal ring electrode 125b.

Figure 9:
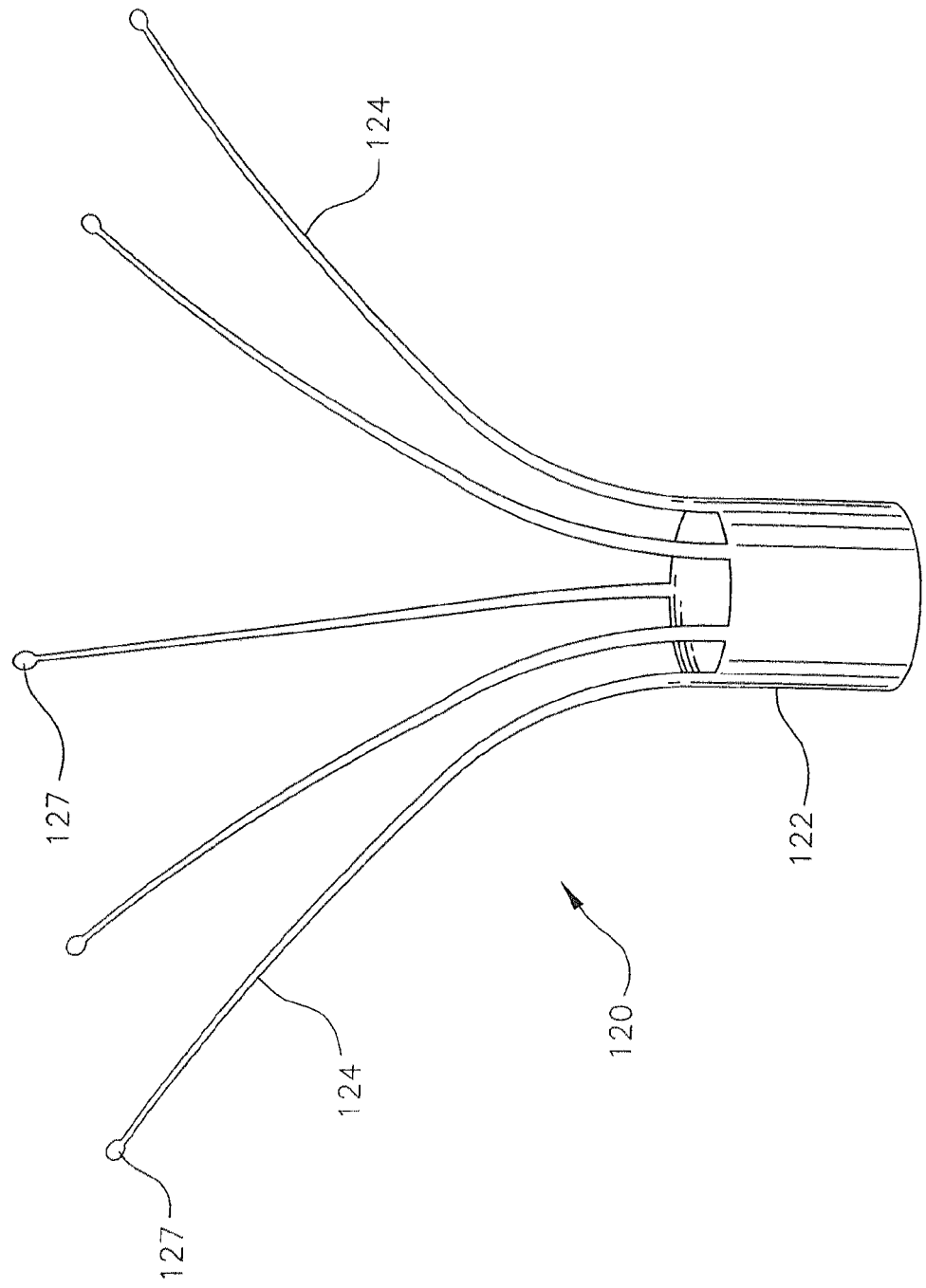
FIG. 9 is a perspective view of a support structure according to the present invention.

In the depicted embodiment, the spines 118 of the mapping assembly 15 are supported and given their desired shape by a support structure 120 comprising a base 122 and plurality of support arms 124 extending from the base, as best shown in FIG. 9. The base 122 of the support structure 120 is generally cylindrically shaped for mounting over the distal end of the tubing 19 of the distal shaft 14. The support arms 124 each have a proximal end attached to the base 122 and a free distal end, as described above. The number of support arms 124 on the support structure corresponds to the desired number of spines 118 on the mapping assembly, and in the depicted embodiment is five.

In a preferred embodiment, the support structure 120 is manufactured from a single metal tube, and thus has a unitary structure. In a particularly preferred embodiment, the support structure 120 is manufactured from a nickel-titanium alloy, for instance, Nitinol. Preferably, the base is a right circular cylinder and has a diameter slightly larger than the distal end of the distal shaft 14.

In the depicted embodiment, each support arm 124 is tapered slightly from its proximal end to its distal end, which allows for greater distal flexibility while maintaining the desired curvature at the proximal end. Each support arm 124 also includes a disc-shaped tip 127, which provides more surface area for the distal end of the support arm 124 to be glued to its corresponding non-conductive covering 134.

During assembly, the base 122 of the support structure 120 is mounted over the distal end of the tubing 19 of the distal shaft 14. Non-conductive coverings 134 are introduced over the support arms 124 to form the spines 118 of the mapping assembly 15. After the ring electrodes 125 are mounted on the spines 118 as described above and the other desired components are assembled within the catheter, a piece of tubular plastic 208 is mounted over the base 122 of the support structure 120 and optionally glued in place. The piece of tubular plastic 208 also covers the proximal ends of the non-conductive coverings 134.

Other methods and structures for forming and supporting the mapping assembly are within the scope of the invention. An example of an alternative design for the mapping assembly according to the invention is described in U.S. patent application Ser. No. 10/040,932, entitled "Catheter Having Multiple Spines Each Having Electrical, Mapping and Location Sensing Capabilities," the disclosure of which is incorporated herein by reference.

In the depicted embodiment, as shown in FIG. 3, the catheter further includes at least one location sensor 140. The location sensor 140 is used to determine the coordinates of the mapping assembly 15 at each instant when the mapping assembly 15 is being used to collect one or more electrical mapping data points. As a result, both electrical and locational data can be obtained for each data point that is mapped. In the depicted embodiment, a single location sensor 140 is mounted in the distal end of the distal shaft 14 within the cylindrical base 122 of the support structure 120. Alternatively, the catheter can include multiple location sensors 140, one mounted within each spine 118 of the mapping assembly 15, as described in U.S. patent application Ser. No. 10/040, 932, entitled "Catheter Having Multiple Spines Each Having Electrical, Mapping and Location Sensing Capabilities," the entire disclosure of which is incorporated herein by reference.

The location sensor 140 is connected to a corresponding sensor cable 74. The sensor cable 74 extends, along with the lead wires 129, through the lead wire lumen 34 of the distal shaft 14, and through the proximal shaft 13 within the protective tube 70 and then into the deflection control handle 16 and out of the proximal end of the deflection control handle within an umbilical cord (not shown) to a sensor control module (not shown) that houses a circuit board (not shown). Alternatively, the circuit board can be housed within the control handle 16, for example, as described in U.S. Pat. No. 6,024,739, the disclosure of which is incorporated herein by reference. The sensor cable 74 comprises multiple wires encased within a plastic covered sheath. In the sensor control module, the wires of the sensor cable 74 are connected to the circuit board. The circuit board amplifies the signal received from the location sensor 140 and transmits it to a computer in a form understandable by the computer by means of a sensor connector at the proximal end of the sensor control module. Also, because the catheter is designed for single use only, the circuit board preferably contains an EPROM chip that shuts down the circuit board approximately twenty-four hours after the catheter has been used. This prevents the catheter, or at least the location sensor 140, from being used twice.

Preferably the location sensor 140 is an electromagnetic location sensor. For example, the location sensor 140 may comprise a magnetic-field-responsive coil, as described in U.S. Pat. No. 5,391,199, or a plurality of such coils, as described in International Publication WO 96/05758. The plurality of coils enables the six-dimensional coordinates (i.e. the three positional and the three orientational coordinates) of the location sensor 140 to be determined. Alternatively, any suitable location sensor known in the art may be used, such as electrical, magnetic or acoustic sensors. Suitable location sensors for use with the present invention are also described, for example, in U.S. Pat. Nos. 5,558,091, 5,443,489, 5,480, 422, 5,546,951, and 5,568,809, International Publication Nos. WO 95/02995, WO 97/24983, and WO 98/29033, and U.S. patent application Ser. No. 09/882,125 filed Jun. 15, 2001, entitled "Position Sensor Having Core with High Permeability Material," the disclosures of which are incorporated herein by reference.

Using this technology, the physician can visually map a heart chamber. This mapping is done by advancing the distal shaft 14 into a heart chamber until contact is made with the heart wall. This position is recorded and saved. The distal shaft 14 is then moved to another position in contact with the heart wall and again the position is recorded and saved.

The location sensor 140 can be used alone or more preferably in combination with the ring electrodes 125. By combining the location sensor 140 and electrodes 125, a physician can simultaneously map the contours or shape of the heart chamber, the electrical activity of the heart, and the extent of displacement of the catheter and hence identify the presence and location of the ischemic tissue. Specifically, the location sensor 125 is used to monitor the precise location of the distal end of the catheter in the heart and the extent of catheter displacement. The ring electrodes 125 are used to monitor the strength of the electrical signals at that location.

The preceding description has been presented with reference to presently preferred embodiments of the invention. Workers skilled in the art and technology to which this invention pertains will appreciate that alterations and changes in the described structure may be practiced without meaningful departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. An injection catheter comprising:
   an elongated catheter body having at least one lumen extending longitudinally therethrough;
   a needle control handle at a proximal end of the catheter body;
   a needle electrode assembly extending through the catheter body and needle control handle and having a proximal end attached to the needle control handle and a distal end within a distal end of the catheter body;
   a mapping assembly, having proximal and distal ends, mounted at the distal end of the catheter body and comprising at least two flexible spines, each spine having a proximal end attached at the distal end of the catheter body and a free distal end, wherein each spine carries at least one electrode; and
   at least one location sensor;
   wherein the distal end of the needle electrode assembly is extendable past the proximal end of the mapping assembly upon manipulation of the needle control handle.

2. The catheter of claim 1, wherein each spine comprises a non-conductive covering having a support arm that has shape memory disposed therein.

3. The catheter of claim 2, wherein each support arm comprises Nitinol.

4. The catheter of claim 1, wherein the mapping assembly is moveable between an expanded arrangement, in which each spine extends radially outward from the catheter body, and a collapsed arrangement, in which each spine is disposed generally along a longitudinal axis of the catheter body.

5. The catheter of claim 4, wherein, when the mapping assembly is in its expanded arrangement, each spine extends radially outwardly from the catheter body and forms an arced shape.

6. The catheter of claim 1, wherein the mapping assembly comprises at least five spines.

7. The catheter of claim 1, further comprising an electrode lead wire having a first end electrically connected to the needle electrode assembly and a second end electrically connected to a source of ablation energy.

8. The catheter of claim 1, wherein the needle electrode assembly comprises a distal tubing having proximal and distal ends and comprising an electrically conductive material and a proximal tubing comprising a material more flexible than the distal tubing and having a distal end attached, directly or indirectly, to the proximal end of the distal tubing.

9. The catheter of claim 8, wherein the distal tubing comprises metal and the proximal tubing comprises plastic.

10. The catheter of claim 8, wherein the distal tubing comprises Nitinol or stainless steel.

11. The catheter of claim 8, wherein the proximal tubing comprises polyimide or PEEK.

12. The catheter of claim 8, wherein the distal end of the distal tubing forms a beveled edge.

13. The catheter of claim 8, wherein the needle electrode assembly further comprises an intermediate tubing joining the proximal and distal tubings.

14. The catheter of claim 8, wherein the needle electrode assembly further comprises an outer plastic tubing fixedly attached, directly or indirectly, to the proximal and distal tubings so that the outer plastic tubing is moveable with the proximal and distal tubings relative to the catheter body.

15. The catheter of claim 14, wherein the electrode lead wire is fixedly attached to the distal tubing and extends within the outer plastic tubing and outside the proximal tubing.

16. The catheter of claim 8, further comprising a temperature sensor mounted within the distal tubing.

17. The catheter of claim 1, further comprising a temperature sensor mounted in or around the needle electrode assembly.

18. An injection catheter comprising:
   an elongated catheter body having at least one lumen extending longitudinally therethrough;
   a needle control handle at a proximal end of the catheter body;
   a needle electrode assembly extending through the catheter body and needle control handle and having a proximal end attached to the needle control handle and a distal end within a distal end of the catheter body; and
   a mapping assembly, having proximal and distal ends, mounted at the distal end of the catheter body and comprising at least two flexible spines, each spine having a proximal end attached at the distal end of the catheter body and a free distal end, wherein each spine carries at least one electrode and at least one location sensor;
   wherein the distal end of the needle electrode assembly is extendable past the proximal end of the mapping assembly upon manipulation of the needle control handle.

19. The catheter of claim 18, wherein each spine comprises a non-conductive covering having a support arm that has shape memory disposed therein.

20. The catheter of claim 18, wherein the mapping assembly is moveable between an expanded arrangement, in which each spine extends radially outward from the catheter body, and a collapsed arrangement, in which each spine is disposed generally along a longitudinal axis of the catheter body.

* * * * *